United States Patent
Hohlbein

(10) Patent No.: US 7,322,067 B2
(45) Date of Patent: Jan. 29, 2008

(54) ORAL CARE IMPLEMENT

(75) Inventor: Douglas J. Hohlbein, Pennington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 11/566,479

(22) Filed: Dec. 4, 2006

(65) Prior Publication Data

US 2007/0101525 A1    May 10, 2007

Related U.S. Application Data

(60) Division of application No. 10/869,922, filed on Jun. 18, 2004, now Pat. No. 7,143,462, and a continuation-in-part of application No. PCT/US03/30633, filed on Sep. 26, 2003, and a continuation-in-part of application No. PCT/US03/29497, filed on Sep. 17, 2003, and a continuation-in-part of application No. 29/189,729, filed on Sep. 10, 2003, now Pat. No. Des. 517,812, which is a continuation-in-part of application No. 10/601,106, filed on Jun. 20, 2003, now abandoned.

(60) Provisional application No. 60/419,425, filed on Oct. 18, 2002, provisional application No. 60/418,776, filed on Oct. 16, 2002, provisional application No. 60/414,117, filed on Sep. 27, 2002, provisional application No. 60/412,290, filed on Sep. 20, 2002.

(51) Int. Cl.
*A46B 9/04* (2006.01)
*A61B 17/24* (2006.01)

(52) U.S. Cl. ............................. 15/111; 15/106; 15/110; 15/167.1; 15/188; 601/141; 606/161

(58) Field of Classification Search .................. 15/106, 15/110, 111, 167.1, 187, 188; 601/139, 141; 606/161; D4/104, 105, 108
See application file for complete search history.

(56) References Cited

U.S. PATENT DOCUMENTS

| 585,358 | A | 6/1897 | Gould |
| 697,338 | A | 4/1902 | Hagarty |
| 726,727 | A | 4/1903 | Mills |
| 864,054 | A | 8/1907 | Abrams |
| 907,842 | A | 12/1908 | Mauzles |
| 1,002,468 | A | 9/1911 | Strangman |
| 1,008,630 | A | 10/1911 | Clarke |
| 1,125,532 | A | 1/1915 | Himmel |
| 1,128,139 | A | 2/1915 | Hoffman |

(Continued)

FOREIGN PATENT DOCUMENTS

CH    99738    6/1923

(Continued)

*Primary Examiner*—Mark Spisich
(74) *Attorney, Agent, or Firm*—Michael J. Wallace

(57) ABSTRACT

An oral care implement with a handle includes a head with a tissue cleanser. The tissue cleanser may be a pad composed of an elastomeric material. The pad is disposed on the head on a surface opposite the tooth cleaning elements. The tissue cleanser may include a plurality of nubs extending for cleaning between the papillae of the tongue. The tissue cleanser may include a plurality of conically shaped nubs. A tissue cleanser can be used to reduce oral malodor problems and remove oral epithelial cells.

21 Claims, 6 Drawing Sheets

U.S. PATENT DOCUMENTS

| | | |
|---|---|---|
| 1,142,698 A | 6/1915 | Crumbaugh |
| 1,163,409 A | 9/1915 | Wheeler |
| 1,191,556 A | 7/1916 | Blake |
| 1,251,250 A | 12/1917 | Libby |
| 1,268,544 A | 6/1918 | Cates |
| 1,470,710 A | 10/1923 | Davis |
| 1,495,675 A | 5/1924 | Coll |
| 1,593,224 A | 8/1926 | Van Sant |
| 1,658,706 A | 2/1928 | Carrott |
| D75,971 S | 8/1928 | Faubert et al. |
| 1,704,564 A | 3/1929 | Friedland |
| 1,705,109 A | 3/1929 | Essbach |
| 1,728,956 A | 9/1929 | Darmitzel |
| 1,741,143 A | 12/1929 | Chin |
| 1,816,582 A | 7/1931 | Heron |
| 1,817,585 A | 8/1931 | Samuel |
| 1,833,555 A * | 11/1931 | Bell et al. ................ 15/188 |
| 1,860,924 A | 5/1932 | Cooke |
| 1,861,347 A | 5/1932 | Johnson |
| 1,872,832 A | 8/1932 | Silverberg |
| 1,891,884 A | 12/1932 | Barrett |
| 1,892,068 A | 12/1932 | Metzler |
| 1,903,161 A | 3/1933 | Barkan |
| 1,993,662 A | 3/1935 | Green |
| 1,993,763 A | 3/1935 | Touchstone |
| D99,352 S | 4/1936 | Grapp |
| 2,042,239 A | 5/1936 | Planding |
| 2,049,958 A | 8/1936 | Greenberg |
| 2,059,914 A | 11/1936 | Rosenberg |
| 2,079,728 A | 5/1937 | Arnold |
| 2,083,217 A | 6/1937 | Brothers et al. |
| 2,129,082 A | 9/1938 | Byrer |
| 2,161,349 A | 6/1939 | Hadden |
| 2,186,005 A | 1/1940 | Casto |
| 2,196,284 A * | 4/1940 | Ackerman ................ 601/139 |
| D122,815 S | 10/1940 | Crosby |
| 2,218,072 A | 10/1940 | Runnals |
| 2,225,331 A | 12/1940 | Campbell |
| 2,233,938 A | 3/1941 | Campbell |
| 2,253,210 A | 8/1941 | Psiharis |
| 2,253,910 A | 8/1941 | Luanz |
| 2,263,602 A | 11/1941 | Grusin |
| 2,305,461 A | 12/1942 | Spyra |
| 2,364,205 A | 12/1944 | Fuller |
| 2,405,029 A | 7/1946 | Gallanty et al. |
| 2,418,485 A | 4/1947 | Shipley |
| 2,491,274 A | 12/1949 | McNeill |
| 2,512,059 A | 6/1950 | Haaussar |
| 2,543,999 A | 3/1951 | Voss |
| D162,941 S | 4/1951 | Ehrman |
| 2,554,777 A | 5/1951 | Dangin |
| 2,574,654 A | 11/1951 | Moore |
| 2,583,750 A | 1/1952 | Runnels |
| 2,642,604 A | 6/1953 | Ferrari |
| 2,651,068 A | 9/1953 | Seko |
| 2,666,325 A | 8/1954 | Silver |
| 2,702,914 A | 3/1955 | Kittle et al. |
| 2,708,762 A | 5/1955 | Kling et al. |
| 3,103,680 A | 9/1963 | Krichmar |
| 3,153,800 A | 10/1964 | Trotin |
| 3,181,193 A | 5/1965 | Nobles et al. |
| 3,195,537 A | 7/1965 | Biasi |
| 3,230,562 A * | 1/1966 | Birch ................ 15/110 |
| 3,254,358 A | 6/1966 | Yao et al. |
| 3,258,805 A | 7/1966 | Rossnan |
| 3,337,893 A | 8/1967 | Fine et al. |
| D213,669 S | 4/1969 | Miller |
| 3,509,674 A | 5/1970 | Stillman |
| 3,610,043 A | 10/1971 | Wemyss |
| 3,633,237 A | 1/1972 | Bagube |
| 4,299,208 A | 11/1981 | Blanc |
| 4,328,604 A | 5/1982 | Adams |
| 4,356,585 A | 11/1982 | Protell et al. |
| 4,364,142 A | 12/1982 | Pangle |
| D272,683 S | 2/1984 | Stocchi |
| D272,687 S | 2/1984 | Stocchi |
| D272,689 S | 2/1984 | Stocchi |
| D272,690 S | 2/1984 | Stocchi |
| D273,635 S | 5/1984 | Stocchi |
| 4,455,704 A | 6/1984 | Williams |
| 4,488,327 A | 12/1984 | Snider |
| 4,610,043 A | 9/1986 | Vezjak |
| D287,072 S | 12/1986 | Pfleger |
| 4,628,564 A | 12/1986 | Youssel |
| D295,695 S | 5/1988 | Golzari |
| 4,827,551 A | 5/1989 | Maser et al. |
| 4,888,844 A | 12/1989 | Maggs |
| D309,528 S | 7/1990 | Valenti |
| 5,005,246 A | 4/1991 | Yen-Hui |
| 5,027,796 A | 7/1991 | Linzey |
| 5,032,082 A | 7/1991 | Herrera |
| 5,040,260 A | 8/1991 | Michaels |
| 5,120,225 A | 6/1992 | Amit |
| 5,165,761 A | 11/1992 | Dirksing |
| 5,176,427 A | 1/1993 | Weihrauch |
| 5,226,197 A | 7/1993 | Nack et al. |
| 5,230,118 A | 7/1993 | Chamma |
| 5,242,235 A | 9/1993 | Li |
| 5,249,327 A | 10/1993 | Hing |
| 5,273,425 A | 12/1993 | Hoagland |
| 5,305,489 A | 4/1994 | Lage |
| D350,851 S | 9/1994 | Spence, Jr. |
| 5,392,483 A | 2/1995 | Heinzelman et al. |
| 5,396,678 A | 3/1995 | Bredall et al. |
| 5,438,726 A | 8/1995 | Leite |
| 5,445,825 A | 8/1995 | Copelan et al. |
| 5,511,273 A | 4/1996 | Carroll |
| 5,530,981 A | 7/1996 | Chen |
| 5,535,474 A | 7/1996 | Salazar |
| 5,570,487 A | 11/1996 | Schneider |
| D376,695 S | 12/1996 | Tveras |
| 5,584,690 A | 12/1996 | Maassarani |
| 5,604,951 A | 2/1997 | Shipp |
| 5,613,262 A | 3/1997 | Choy-Maldonado |
| 5,628,082 A | 5/1997 | Moskovich |
| D386,905 S | 12/1997 | Brady et al. |
| 5,709,004 A | 1/1998 | Paduano et al. |
| D390,706 S | 2/1998 | Hohlbein et al. |
| D391,769 S | 3/1998 | Kling et al. |
| 5,735,011 A | 4/1998 | Asher |
| 5,735,864 A | 4/1998 | Heisinger, Jr. |
| 5,758,380 A | 6/1998 | Vrignaud |
| 5,766,193 A | 6/1998 | Millner |
| D396,288 S | 7/1998 | Samuel |
| 5,778,475 A | 7/1998 | Garcia |
| 5,778,476 A | 7/1998 | Squillaci et al. |
| 5,779,654 A | 7/1998 | Foley et al. |
| D397,219 S | 8/1998 | Rangel et al. |
| 5,792,159 A | 8/1998 | Amin |
| 5,802,656 A | 9/1998 | Dawson et al. |
| 5,810,856 A | 9/1998 | Tveras |
| D399,349 S | 10/1998 | Barth |
| 5,817,114 A | 10/1998 | Anderson et al. |
| 5,818,856 A | 10/1998 | Injeyan et al. |
| D401,069 S | 11/1998 | Lamond et al. |
| D402,116 S | 12/1998 | Magloff et al. |
| 5,842,247 A | 12/1998 | Decesare et al. |
| 5,845,358 A | 12/1998 | Woloch |
| D403,510 S | 1/1999 | Menke et al. |
| D404,205 S | 1/1999 | Hohlbein |
| D404,206 S | 1/1999 | Hohlbein |
| D405,272 S | 2/1999 | Khalaj et al. |
| D407,221 S | 3/1999 | Van Gelder |
| D407,222 S | 3/1999 | Van Gelder |

| | | |
|---|---|---|
| D407,223 S | 3/1999 | Van Gelder |
| 5,875,510 A | 3/1999 | Lamond et al. |
| 5,896,614 A | 4/1999 | Flewitt |
| 5,913,346 A | 6/1999 | Narwani |
| 5,915,433 A | 6/1999 | Hybler |
| 5,920,941 A | 7/1999 | Iannotta |
| 5,928,254 A | 7/1999 | Jensen |
| 5,930,860 A | 8/1999 | Shipp |
| 5,938,673 A | 8/1999 | DePierro et al. |
| 5,946,759 A | 9/1999 | Cann |
| 5,951,578 A | 9/1999 | Jensen |
| 5,957,942 A | 9/1999 | Yudelman |
| 5,967,152 A | 10/1999 | Rimkus |
| 5,970,564 A | 10/1999 | Inns et al. |
| 5,980,541 A | 11/1999 | Tenzer |
| 5,980,542 A | 11/1999 | Saldivar |
| 5,984,935 A | 11/1999 | Welt et al. |
| 6,015,293 A | 1/2000 | Rimkus |
| D420,515 S | 2/2000 | Van Gelder |
| D421,844 S | 3/2000 | Stark et al. |
| 6,032,315 A | 3/2000 | Liebel |
| 6,041,467 A | 3/2000 | Roberts et al. |
| D422,413 S | 4/2000 | Goldinger et al. |
| D423,785 S | 5/2000 | Karallis |
| D423,786 S | 5/2000 | Zelinski |
| D423,787 S | 5/2000 | Musciano |
| D424,808 S | 5/2000 | Beals et al. |
| D424,809 S | 5/2000 | Bernard |
| D425,306 S | 5/2000 | Beals et al. |
| 6,058,541 A | 5/2000 | Masterman et al. |
| D428,702 S | 8/2000 | Van Gelder |
| 6,098,233 A | 8/2000 | Chen |
| 6,105,191 A | 8/2000 | Chen et al. |
| 6,108,851 A | 8/2000 | Bredall et al. |
| 6,108,869 A | 8/2000 | Meessmann et al. |
| 6,119,296 A | 9/2000 | Noe et al. |
| 6,131,228 A | 10/2000 | Chen et al. |
| D434,906 S | 12/2000 | Beals et al. |
| 6,171,323 B1 | 1/2001 | Potti et al. |
| D440,767 S | 4/2001 | Moskovich et al. |
| 6,254,390 B1 | 7/2001 | Wagner |
| 6,260,227 B1 | 7/2001 | Fulop et al. |
| 6,278,021 B1 | 8/2001 | Hohlbein |
| 6,289,545 B1 | 9/2001 | Molster |
| D448,569 S | 10/2001 | Harris et al. |
| 6,322,573 B1 | 11/2001 | Murayama |
| 6,345,405 B1 | 2/2002 | Brackin |
| 6,352,545 B1 | 3/2002 | Wagner |
| 6,353,958 B2 | 3/2002 | Weihrauch |
| RE37,625 E | 4/2002 | Wieder et al. |
| D456,139 S | 4/2002 | Hohlbein |
| 6,374,448 B2 | 4/2002 | Seifert |
| D456,607 S | 5/2002 | Carlucci et al. |
| 6,383,202 B1 | 5/2002 | Rosenblood |
| D459,087 S | 6/2002 | Pfleger |
| 6,402,768 B1 | 6/2002 | Liebel |
| 6,408,476 B1 | 6/2002 | Cann |
| 6,421,867 B1 | 7/2002 | Weihrauch |
| D461,959 S | 8/2002 | Chan et al. |
| D463,131 S | 9/2002 | Winter et al. |
| 6,446,295 B1 | 9/2002 | Calabrese |
| D464,796 S | 10/2002 | Winter et al. |
| 6,463,619 B2 | 10/2002 | Gavney, Jr. |
| D465,847 S | 11/2002 | Jacobs |
| 6,496,999 B1 | 12/2002 | Gleason et al. |
| 6,513,182 B1 | 2/2003 | Calabrese et al. |
| D471,276 S | 3/2003 | Potti |
| 6,546,586 B2 | 4/2003 | Cho |
| D477,465 S | 7/2003 | Reilly et al. |
| D478,211 S | 8/2003 | Ping |
| 6,625,839 B2 | 9/2003 | Fischer |
| D482,199 S | 11/2003 | De Salvo |
| 6,647,581 B1 | 11/2003 | Persad et al. |
| D483,184 S | 12/2003 | Geiberger et al. |
| D483,568 S | 12/2003 | Jamson |
| D486,649 S | 2/2004 | Sprosta et al. |
| 6,729,789 B2 | 5/2004 | Gordon |
| 6,817,054 B2 | 11/2004 | Moskovich et al. |
| 6,859,969 B2 | 3/2005 | Gavney et al. |
| D503,538 S | 4/2005 | De Salvo |
| 6,886,207 B1 | 5/2005 | Solanki |
| 6,895,629 B1 | 5/2005 | Wenzler |
| 2001/0023518 A1 | 9/2001 | Driesen et al. |
| 2001/0041903 A1 | 11/2001 | Richard |
| 2001/0042280 A1 | 11/2001 | Moskovitch et al. |
| 2002/0004964 A1 | 1/2002 | Luchino et al. |
| 2002/0019645 A1 | 2/2002 | Fischer et al. |
| 2002/0108194 A1 | 8/2002 | Carlucci et al. |
| 2002/0124333 A1 | 9/2002 | Haffiger et al. |
| 2002/0124337 A1 | 9/2002 | Calabrese et al. |
| 2002/0138926 A1 | 10/2002 | Brown, Jr. et al. |
| 2002/0138928 A1 | 10/2002 | Calabrese |
| 2003/0009837 A1 | 1/2003 | Cann |
| 2003/0115699 A1 | 6/2003 | Wagstaff |
| 2003/0116884 A1 | 6/2003 | Wagstaff |
| 2003/0163149 A1 | 8/2003 | Heisinger, Jr. |
| 2003/0167582 A1 | 9/2003 | Fischer, Jr. |
| 2003/0196283 A1 | 10/2003 | Gatzemeyer et al. |
| 2003/0208865 A1 | 11/2003 | Davies |
| 2003/0216762 A1 | 11/2003 | Levtl |
| 2003/0229959 A1 | 12/2003 | Kim et al. |
| 2004/0006837 A1 | 1/2004 | Cann |
| 2004/0025275 A1 | 2/2004 | Moskovich et al. |
| 2004/0068610 A1 | 4/2004 | Lee |
| 2004/0134007 A1 | 7/2004 | Davies |
| 2004/0200748 A1 | 10/2004 | Klassen et al. |
| 2004/0255416 A1 | 12/2004 | Hohlbein |
| 2005/0000049 A1 | 1/2005 | Hohlbein |
| 2005/0069372 A1 | 3/2005 | Hohlbein et al. |

FOREIGN PATENT DOCUMENTS

| | | |
|---|---|---|
| CN | 99225704.2 | 11/1999 |
| DE | 857 128 | 11/1952 |
| DE | 29 30 459 | 2/1981 |
| DE | 31 14 507 A1 | 3/1983 |
| DE | 36 39 424 A1 | 6/1988 |
| EP | 0 875 169 | 11/1998 |
| EP | 1 034 721 | 9/2000 |
| EP | 1308108 | 5/2003 |
| FR | 537979 | 6/1922 |
| FR | 2594307 A1 | 4/1987 |
| GB | 17643 | 0/1912 |
| GB | 495982 | 11/1938 |
| GB | 2371217 | 7/2002 |
| GB | 2391462 | 2/2004 |
| JP | 2000-278899 | 10/2000 |
| JP | 2000-308522 | 11/2000 |
| JP | 2001-314232 | 11/2001 |
| JP | 2002-142867 | 5/2002 |
| SU | 1708283 | 1/1992 |
| WO | WO 98/05241 A | 2/1998 |
| WO | WO 98/08458 | 3/1998 |
| WO | WO 98/09573 | 3/1998 |
| WO | WO 99/49754 A1 | 10/1999 |
| WO | WO 00/53054 | 9/2000 |
| WO | WO 00/64307 | 11/2000 |
| WO | WO 01/17433 A1 | 3/2001 |
| WO | WO 01/45573 A1 | 6/2001 |
| WO | WO 01/80688 A2 | 11/2001 |
| WO | WO 02/062174 | 8/2002 |
| WO | WO 02/071967 A2 | 9/2002 |
| WO | WO 03/030680 A | 4/2003 |
| WO | WO 2004/019801 A | 3/2004 |

* cited by examiner

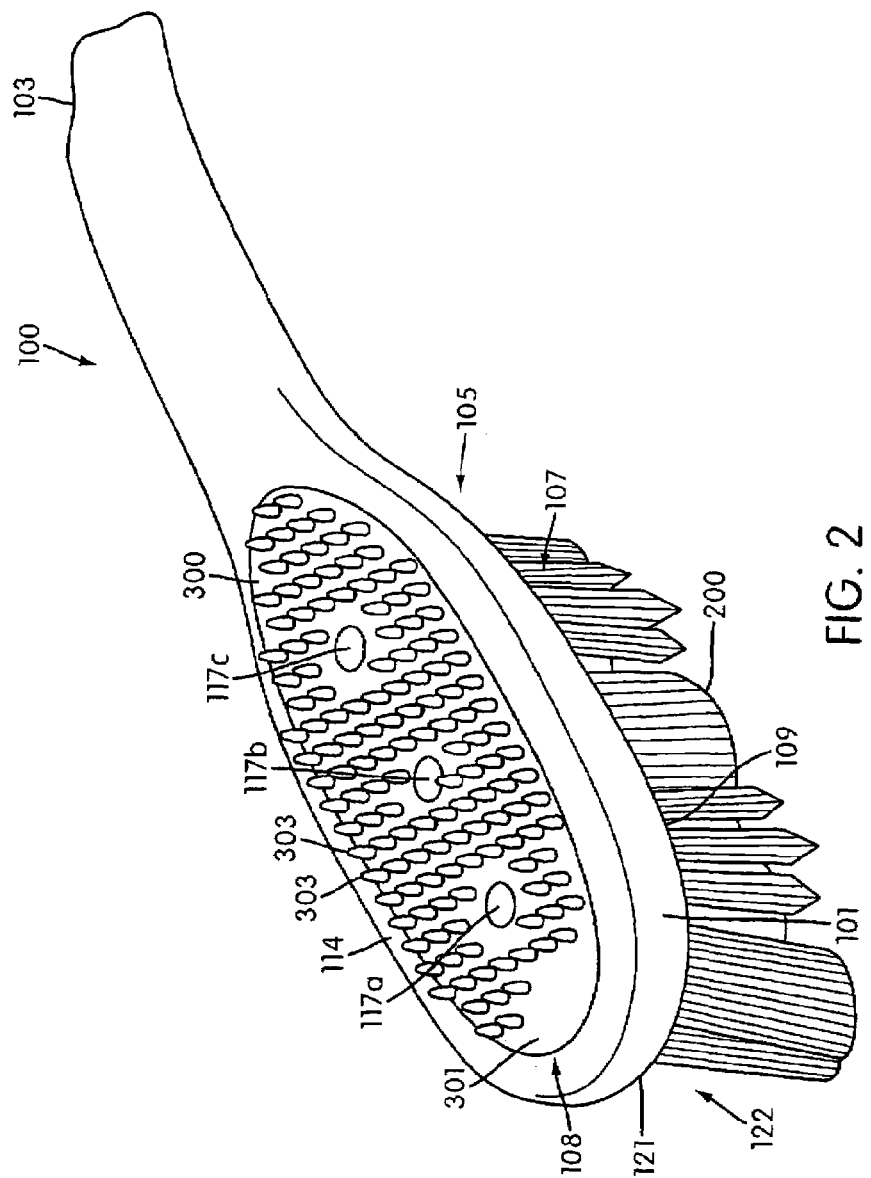

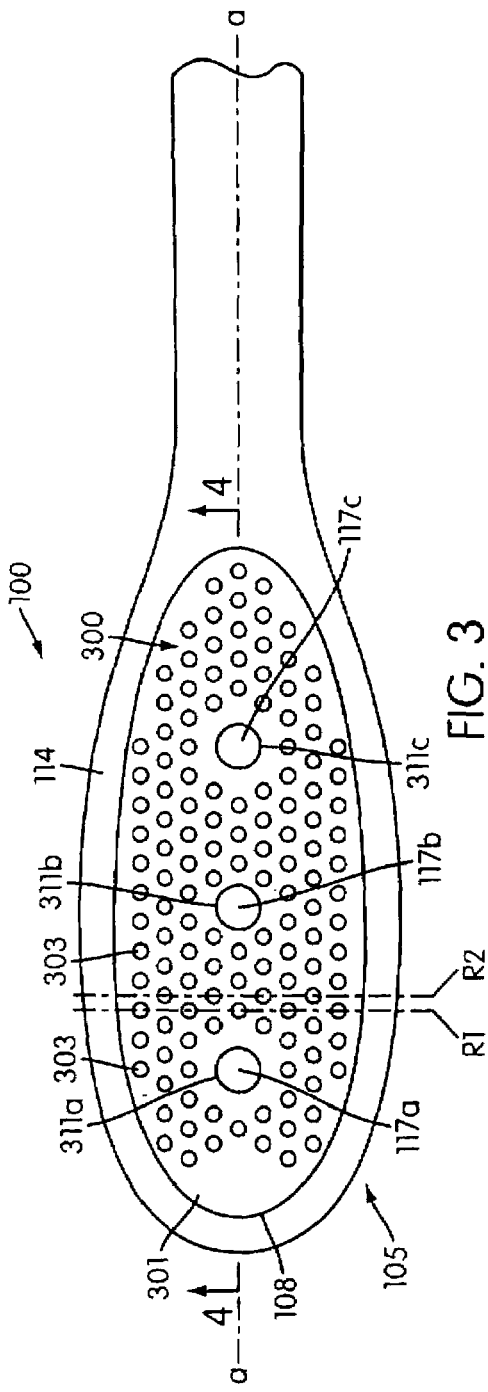
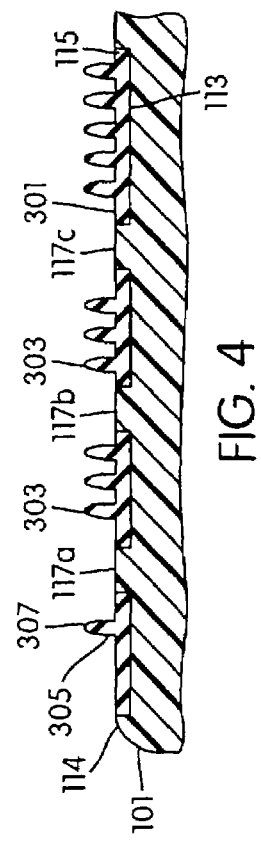

ORAL CARE IMPLEMENT

CROSS-REFERENCE TO RELATED APPLICATIONS

This application is a divisional application of U.S. patent application Ser. No. 10/869,922, filed Jun. 18, 2004, now U.S. Pat. No. 7,143,462 which is a continuation in part of U.S. patent application Ser. No. 10/601,106 filed Jun. 20, 2003, now abandoned entitled "Toothbrush with Tongue Cleaning Member", and a continuation-in-part of PCT Patent Application Serial No. PCT/US03/030633 filed Sep. 26, 2003, entitled "Toothbrush" (now abandoned), which claims the benefit of priority to U.S. Provisional Application No. 60/414,117, filed Sep. 27, 2002, (now abandoned) U.S. Provisional Application No. 60/418,776, filed Oct. 16, 2002 (now abandoned) and U.S. Patent Application No. 60/419,425, filed Oct. 18, 2002 (now abandoned) and a continuation-in-part of PCT Patent Application No. PCT/US2003/029497, filed Sep. 17, 2003, entitled "Toothbrush With Gripping Area (now abandoned), which claims the benefit of priority to U.S. Provisional Patent Application Ser. No. 60/412,290, filed Sep. 20, 2002 (now abandoned), and is a continuation in part of U.S. patent application Ser. No. 29/189,729, filed Sep. 10, 2003, Now U.S. Patent No. D517,812. This divisional application is also related to U.S. patent application Ser. No. 10/870,462 entitled "Toothbrush" filed on Jun. 18, 2004, now U.S. Pat. No. 7,086,621, in which the contents was incorporated by reference in said U.S. patent application Ser. No. 10/869,922. The contents of the above-noted applications are each expressly incorporated herein by reference.

FIELD OF THE INVENTION

The present invention pertains to an oral care implement with a cleanser for cleaning soft tissue surfaces in the mouth.

BACKGROUND OF THE INVENTION

According to the American Dental Association, a major source of bad breath in healthy people is microbial deposits on the tongue, where a bacterial coating harbors organisms and debris that contribute to bad breath. The tongue is a haven for the growth of microorganisms since the papillary nature of the tongue surface creates a unique ecological site that provides an extremely large surface area, favoring the accumulation of oral bacteria. Anaerobic flora and bacteria residing on the tongue play an important role in the development of chronic bad breath commonly called halitosis. In general, the bacteria produce volatile sulfur compounds (VSC). If there is enough buildup of the sulfur compounds, the result can be lead bad breath or oral malodor.

While bladed tongue scrapers have been used in the past, these scrapers are inadequate in respect to their effectiveness on the soft tissue surface of the tongue. Broad flat scraping blades are limited in their ability to reach between the papillae where the bacteria and microdebris have collected. Moreover, notwithstanding the benefits to be gained by any ability to clean the tongue, some users avoid the use of such blades because of lack of comfort on the tongue surface.

Hence, there is a need for an oral care implement with a tongue cleanser that provides effective removal of the tongue bacteria and other debris while maintaining comfort to the user.

BRIEF SUMMARY OF THE INVENTION

The invention pertains to an oral care implement with a tissue cleanser that provides improved cleaning and effective removal of bacteria and microdebris disposed on the oral tissue surfaces.

In one aspect of the invention, the tissue cleanser includes a plurality of nubs for cleaning soft tissue surfaces in the mouth and particularly for cleaning between the papillae of the tongue. In a further preferred aspect of the invention, the tissue cleanser includes a plurality of conically shaped nubs.

In another aspect of the invention, the tissue cleanser is constructed from an elastomeric material. In one preferred embodiment, the tissue cleanser is formed as an elastomeric pad mounted on the head of the oral care implement for improved cleaning, ease of manufacture, and user comfort.

In another aspect of the invention, the oral care implement includes a seat to facilitate and ease molding of the tissue cleanser to the head. In one preferred construction, the head has one or more protuberances for anchoring the head during molding of the tissue cleanser. The head may also include a basin to further define the outline of the molded tissue cleanser.

In another aspect of the invention, an oral care implement includes a tissue cleanser having means for reducing oral volatile sulfur compounds by 35% from a baseline measured two hours after use.

In another aspect of the invention, an oral care implement is provided with tooth cleaning elements and a tissue cleanser for a thorough cleaning of the teeth, gums, tongue and oral surfaces of the cheeks and lips. In a preferred construction, the tooth cleaning elements and tissue cleanser are supported on opposite sides of a supporting head.

In one other aspect of the invention, an oral care implement which includes tooth cleaning elements and a tissue cleanser forms at least one of the tooth cleaning elements as a unitary member with the tissue cleanser.

BRIEF DESCRIPTION OF THE DRAWINGS

A more complete understanding of the present invention and the advantages thereof may be acquired by referring to the following description in consideration of the accompanying drawings, in which like reference numbers indicate like features, and wherein:

FIG. 2 is an enlarged perspective view of a head of an oral care implement of FIG. 1;

FIG. 3 is a plan view of the oral care implement of FIG. 1 illustrating a tongue cleaning feature;

FIG. 4 is a partial section view of a head of the oral care implement of FIG. 1 taken along line 4-4 of FIG. 3;

DETAILED DESCRIPTION OF THE INVENTION

Figure 1:
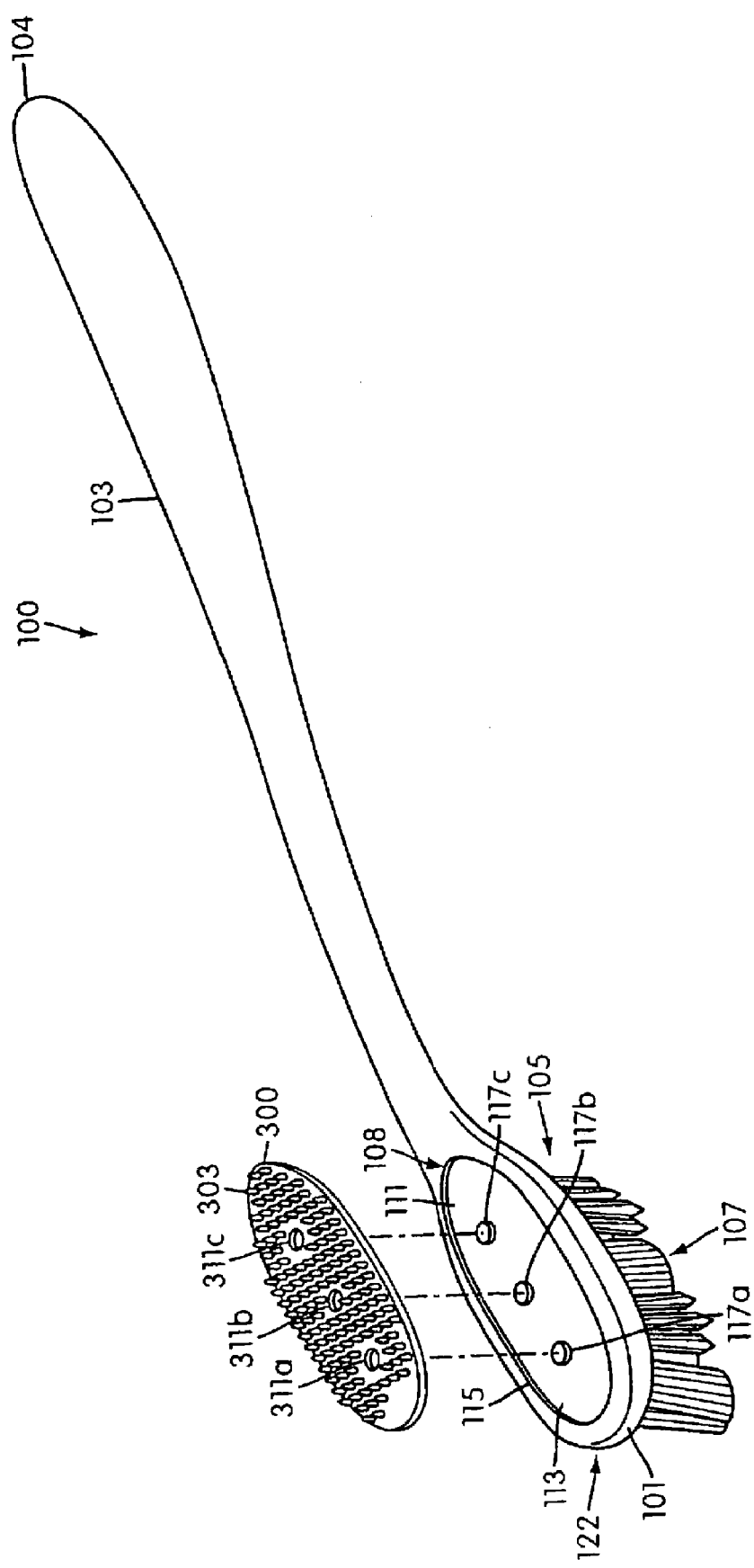
FIG. 1 is an exploded assembly perspective view of an oral care implement according to one or more aspects of an illustrative embodiment.

In the following description, the invention is discussed in terms of a toothbrush, but could be in the form of other oral care implements including simply a tissue cleansing implement. Further, it is to be understood that other embodiments may be utilized and structural and functional modifications may be made without departing from the scope of the present invention.

FIGS. 1-7 illustrate an oral care implement, such as a toothbrush 100, having a handle 103 and a head 105 which may be used for cleaning the teeth and soft tissue in the mouth, such as the tongue, interior surfaces of the cheeks, lips or the gums. Handle 103 is provided for the user to readily grip and manipulate the toothbrush, and may be formed of many different shapes and constructions. While the head is normally widened relative to the neck of the handle, it could in some constructions simply be a continuous extension or narrowing of the handle. In the preferred construction, head 105 has a first face 106 that supports tooth cleaning elements 107 (FIGS. 5 and 6) and a second face 108 that supports a tissue cleanser 300 (FIGS. 2 and 3). The first and second faces 106, 108 are preferably on opposite sides of head 105. Nevertheless, tissue cleanser 300 may be mounted elsewhere, such as the proximal end 104 of handle 103. The tissue cleanser 300 or portions of it may also be located on the peripheral sidewall surface 101 of head 105 or extend farther towards the proximate end 104 of handle 103 than illustrated.

The elastomeric material of tissue cleanser 300 may be any biocompatible resilient material suitable for uses in an oral hygiene apparatus. To provide optimum comfort as well as cleaning benefits, the elastomeric material preferably has a hardness property in the range of A8 to A25 Shore hardness. As an example, one preferred elastomeric material is styrene-ethylene/butylene-styrene block copolymer (SEBS) manufactured by GLS Corporation. Nevertheless, SEBS material from other manufacturers or other materials within and outside the noted hardness range could be used.

Tissue cleanser 300 is preferably configured with a multiplicity of tissue engaging elements 303 (FIGS. 1-4), which in the preferred construction are formed as nubs. As used herein a "nub" is generally meant to include a column-like protrusion (without limitation to the cross-sectional shape of the protrusion) which is upstanding from a base surface. In a general sense, the nub, in the preferred construction, has a height that is greater than the width at the base of the nub (as measured in the longest direction). Nevertheless, nubs could include projections wherein the widths and heights are roughly the same or wherein the heights are somewhat smaller than the base widths. Moreover, in some circumstances (e.g., where the nub tapers to a tip or includes a base portion that narrows to a smaller projection). The base width can be substantially larger than the height.

Such tissue engaging elements 303 are designed to significantly reduce a major source of bad breath in people and improve hygiene. Nubs 303 enable removal of microflora and other debris from the tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise pulled against a tongue surface, for example, nubs 303 of elastomeric tissue cleanser 300 provide for gentle engagement with the soft tissue while reaching downward into the recesses of adjacent papillae of the tongue. The elastomeric construction of tissue cleanser 300 also enables the base surface 301 to follow the natural contours of the oral tissue surfaces, such as the tongue, cheeks, lips, and gums of a user.

Moreover, the soft nubs 303 are able to flex as needed to traverse and clean the soft tissue surfaces in the mouth along which it is moved.

As seen in FIG. 2 and 4, in one preferred arrangement of tissue cleanser 300, nubs 303 are preferably conically shaped. As used herein, "conically shaped" or "conical" is meant to include true cones, frusto-conically shaped elements, and other shapes that taper to a narrow end and thereby resemble a cone irrespective of whether they are uniform, continuous in their taper, or have rounded cross-sections. With reference to FIG. 4, the base portion 305 of each conically shaped tissue engaging element 303 is larger than the corresponding tip portion 307. In this conically shaped configuration, the base portion 305 has a wider cross-sectional area to provide effective shear strength to withstand the lateral movement of the tissue cleanser 300 along the surface of the tongue or other soft tissue surface. The smaller width or diameter of the tip portion 307 in conjunction with the length of the conically shaped nub 303 enable the nubs to sweep into the recesses of the tongue and other surfaces to clean the microbial deposits and other debris from the soft tissue surfaces. In the preferred construction, nubs 303 are able to flex and bend from their respective vertical axes as lateral pressure is applied during use. This flexing enhances the comfort and cleaning of the soft tissue surfaces. In a preferred construction, the thickness or width of the base of the nub in 0.64 mm, and preferably within the range from about 0.51 mm to about 2.00 mm. Tip 307 of the nubs is 0.127 mm and preferably within that range from about 0.10 mm to about 0.75 mm for optimal penetration between the recesses of papillae of a user's tongue. The length or height of nubs 303, as measured from base surface 301 to tip 307, is preferably 0.91 mm and preferably within range from about 0.5 mm to about 2.5 mm, and most preferably range between 0.75 mm to 1.5 mm. Nevertheless, nubs of other sizes and shapes outside the given ranges can be used.

Alternatively, the tissue cleaning elements 303 may have other shapes. As one example, the tissue cleanser may have a grated form such as described in co-pending U.S. patent application Ser. No. 10/601,106, incorporated herein by reference.

In a preferred construction, nubs 303 are disposed on the base surface 301 of tissue cleanser 300 in a high density pattern. Each nub 303 is preferably spaced apart from adjacent nubs 303 between a range of about 0.5 mm to about 3 mm; more preferably the spacing ranges between 0.7 mm to 2.5 mm, and most preferably between 1 mm to 2 mm. Nevertheless, other spacing ranges are possible. The surface density of the nubs 303 on base surface 301 ranges preferably from about 100 to about 600 nubs per square inch. In a more preferred construction of the tissue cleanser, the surface density may range from 200 to 500 nubs per square inch, and most preferably between 300 to 450 nubs per square inch. In one preferred example, tissue cleanser 300 includes about 400 nubs per square inch of surface area. The surface density features in conjunction with the height of the nubs 303 enables the tissue cleanser to provide enhanced cleaning of the soft tissue surfaces with improved comfort. Nonetheless, other surface densities are possible.

As seen in FIG. 3, nubs 303 are preferably disposed in longitudinal rows in a direction generally parallel to the longitudinal axis a-a. Further, nubs 303 are disposed in transverse rows R1, R2 on an axis parallel to base surface 301 and generally perpendicular to the longitudinal axis a-a. In one preferred construction, adjacent nubs 303 are provided on the base surface 301 in a staggered arrangement.

For example, adjacent transverse rows of nubs R1 and R2 have nubs 303 that are not directly behind each other. A first nub is said herein to be "directly behind" second nub when it is located within the lateral bounds of the second nub extending in a longitudinal direction. This configuration enables improved cleaning of the soft tissue surfaces by facilitating the removal of microflora and other debris, and especially from the recesses of adjacent papillae of the tongue. Nonetheless, the nubs could be arranged randomly or in a myriad of different patterns.

Tongue cleanser 300 is preferably formed by being molded to head 105, although other manufacturing processes could be used. With reference to FIGS. 1 and 4, tissue cleanser 300 is preferably molded within a basin or a receiving cavity 111 in face 108 of head 105. The receiving cavity 111 has a lower base surface 113 and a peripheral sidewall 115 extending away from the lower base surface 113. In one mounting arrangement, nubs 303 of the tissue cleanser 300 are exposed for use with the base surface of the tissue cleanser 300 being flush or recessed relative to the surface 114 of the head. Nevertheless, other orientations are possible. Also, base surface 301 of the tissue cleanser could be embedded in head 105 or covered by another layer with nubs 303 projecting through appropriate openings.

As can be seen in FIGS. 1 and 4, face 108 also preferably includes one or more peg members 117a-c disposed within basin 111. Peg members 117 form anchor points against the opposing mold to prevent the head from moving under the pressure of the injection molding. As a result, tissue cleanser 300 preferably includes one or more complementary apertures 311a-c which exposes the tops of peg members 117a-c. Although, the pegs are illustrated in alignment along the centerline of the head (e.g. longitudinal axis a-a), the pegs could have many different positions. Further, the pegs and basin are preferably both included with head 105, but either could be used without the other.

Alternatively, basin 111 and peg members 117a-c may be provided to position and hold a previously molded tissue cleanser, although these constructions are not necessary to use such a previously molded tissue cleanser.

Peg members 117a-c may take on a variety of shapes and lengths. With continued reference to the FIGS. 1 and 4, head 105 includes peg members 117a-c extending away from the lower base surface 113 of basin 111 to the height of the peripheral sidewall 115. The peg members 117a-c are shaped in the form of a cylinder, but other shapes and lengths of the peg members 117a-c are possible. While the molding process would preferably bond the tissue cleanser to the head, the tissue cleanser could be performed and attached by adhesive or other known means.

As shown in FIGS. 1-4, tissue cleanser 300 is preferably formed as a pad composed of a soft and pliable elastomeric material for comfortable cleaning and effective removal of bacteria and debris disposed on the surface of the tongue, other soft tissue in the mouth and even along the lips. The tissue cleanser 300 also provides effective massaging, stimulation and removal of bacteria, debris and epithelial cells from the surfaces of the tongue, cheeks, gums or lips.

In the preferred construction (FIGS. 1-6), tissue cleansers 300 may rub against the inside surfaces of the cheeks or lips, and on the sides of the tongue while the user brushes his or her teeth, and thus provide a desired massaging, stimulation and cleaning of various soft tissue surfaces within the mouth. For example, during brushing of the facial tooth surfaces, tissue cleanser 300 is disposed on the outer face 108 of head 105 to naturally rub against the oral surfaces of the cheek. As a result, enhanced cleaning is attained without additional cleaning steps. Further, some users may sense a stimulating tingle on the cheek surfaces that leads to a positive user reaction, and even enjoyment of the comfortable feel of the tissue cleanser along the soft tissues surfaces in the mouth. Tissue cleanser 300 may also be additionally rubbed on the cheeks, tongue, etc. as desired for further cleaning aside from the contact that may occur while brushing the teeth.

Figure 5:
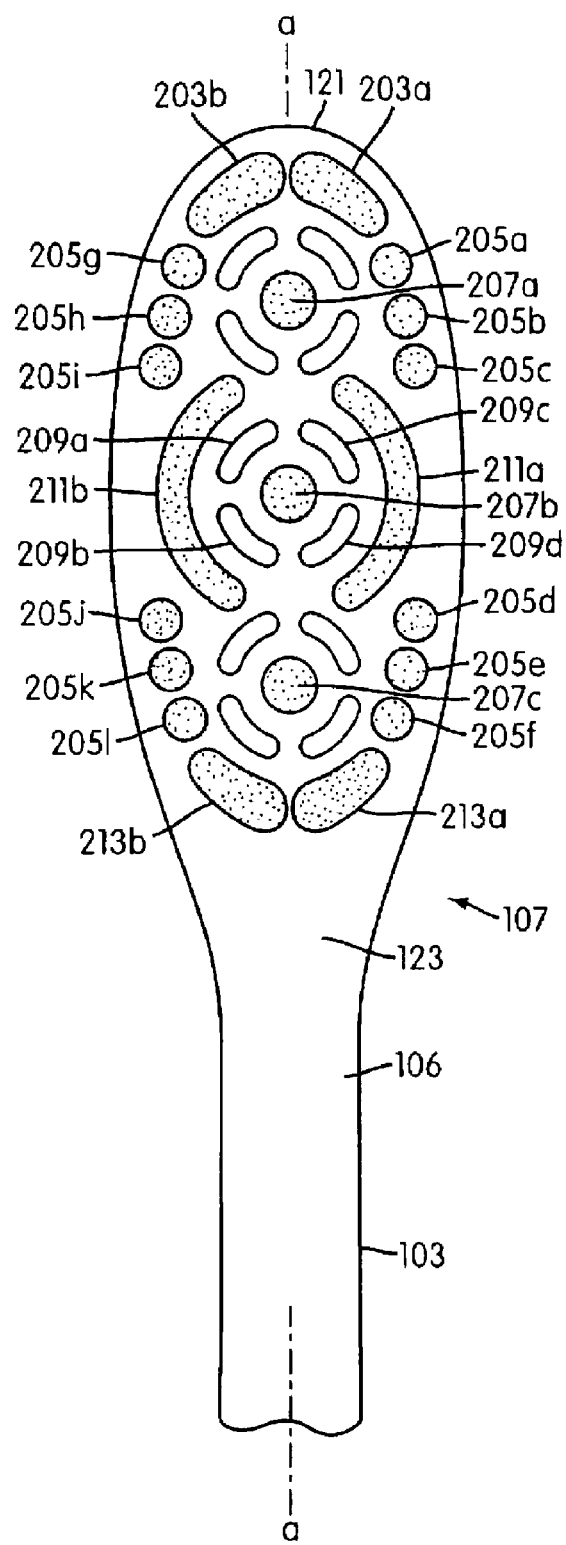
FIG. 5 is a plan view of the oral care implement of FIG. 1 illustrating at least one tooth cleaning configuration.
Figure 6:
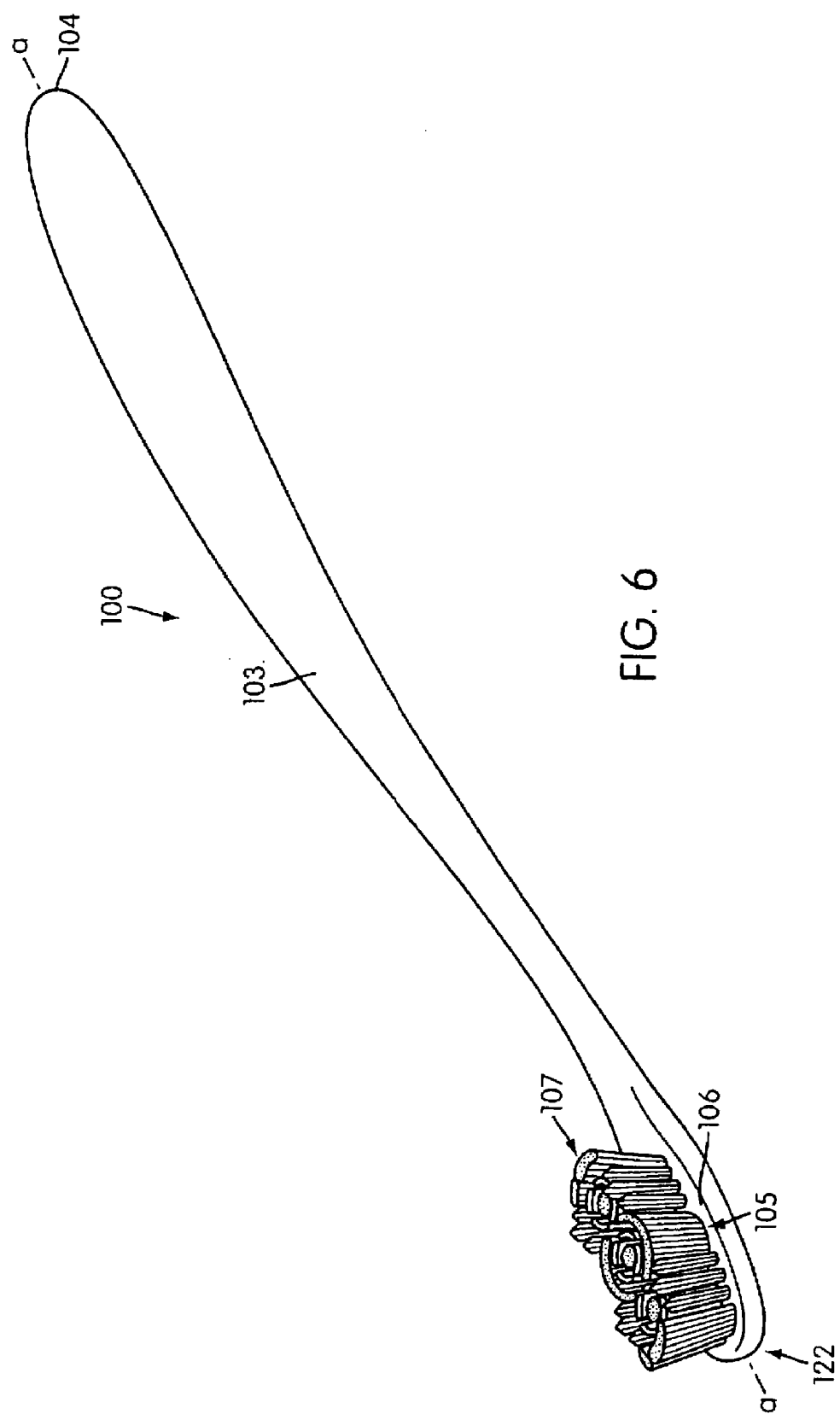
FIG. 6 is a perspective of the view of the oral care implement illustrating example tooth cleaning elements.

Referring to FIGS. 5 and 6, the tooth cleaning elements 107 of head 105 may include a variety of tooth cleaning elements which can be used for wiping, cleaning and massaging the user's teeth and gums. Any suitable form of tooth cleaning elements may be used. The term "tooth cleaning elements" is used in a generic sense which refers to filament bristles or elastomeric fingers or walls that have any desirable shape. In the illustrated example of FIG. 5, tooth cleaning elements 107 include distal tooth cleaning elements 203a-b disposed at a distal tip 121 of head 105, peripheral tooth cleaning elements 205a-l, longitudinal tooth cleaning elements 207a-c disposed along longitudinal axis a-a, arcuate tooth cleaning elements 209a-d and 211a-b, and proximal cleaning elements 213a, b. Tooth cleaning elements 205, 207, 211 and 213 are preferably provided as tufts of bristles whereas tooth cleaning elements 209 are preferably formed as elastomeric walls. Nevertheless, other forms and types of tooth cleaning elements may be used.

Figure 7:
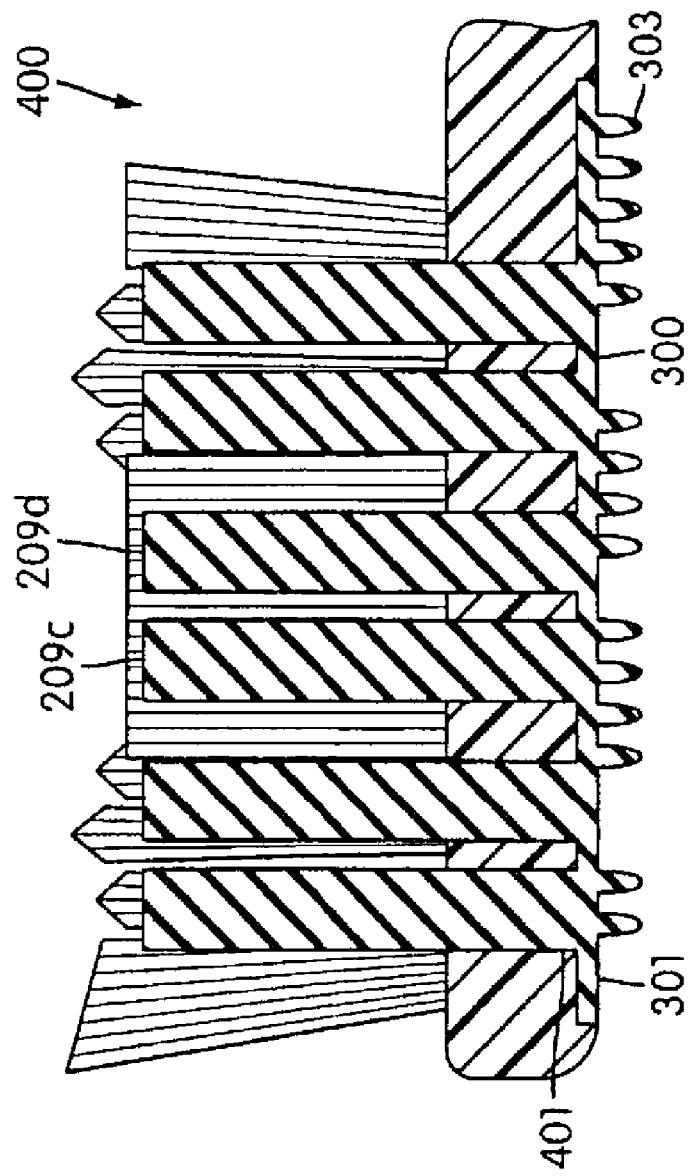
FIG. 7 is a section view of an alternative construction of the head of an oral care implement.

FIG. 7 illustrates a sectional view of an alternative arrangement of a head 400 of a toothbrush. Head 400 is similar in construction to head 105, except that tooth cleaning elements 209a-d are integrally formed with tissue cleanser 300. To accomplish the alternative construction, head 400 has appropriately sized ports or openings 401 to allow the elastomeric material to flow through the head during an injection molding process. In this construction, tooth cleaning elements 209a-d and tissue cleaner 300 are formed with the same elastomeric material. Thus, head 400 may include at least one elastomeric tooth cleaning element formed as a unitary member with tissue cleanser 300.

As various changes could be made in the above methods, compositions and structures without departing from the scope of the invention, it is intended that all matter contained in this application, including all mechanisms and/or modes of interaction described above, shall be interpreted as illustrative only and not limiting in any way the scope of the appended claims.

The following examples are set forth as representative of the improved operation of the present invention. These examples are not to be construed as limiting the scope of the invention.

EXAMPLE 1

The performance nature of a toothbrush can be measured using known oral malodor assessment methods. A study was conducted to evaluate the performance of a toothbrush provided with an elastomeric tissue cleanser having conically shaped nubs, such as the preferred construction of toothbrush 100 discussed above. Human test subjects participated in the study. There was a washout or normalization period prior to testing of about 7 days in which the test subjects brushed twice a day with a fluoride dental cream (see Table 1). After the washout period, the test subjects were asked to refrain from any oral hygiene (brushing, rinsing, and flossing), eating and drinking prior to oral testing. A baseline volatile sulfur compound (VSC) sample was taken from each of the test subjects. In the study for overnight odor control, the test subjects brushed their teeth for one minute with a fluoride dental cream (see Table 1) using toothbrush 100 provided with the above noted tissue cleanser 300. Subsequently, the subjects cleaned their tongue surface with the tissue engaging elements of the toothbrush for ten seconds. The test subjects slept overnight and returned for post treatment. VSC samples were taken at the ten-hour time point from the previous day cleaiung. In the illustrative example, use of the toothbrush reduced oral VSC about 60% verses brushing the teeth alone as measured from a baseline ten hours after use. The VSC readings were obtained by gas chromatography.

EXAMPLE 2

In another study of the above-noted toothbrush 100, there was a washout or normalization period prior to testing of about 7 days which the test subjects brushed twice a day with a fluoride dental cream (see Table 1). The test subjects were asked to refrain from any oral hygiene (brushing, rinsing, and flossing), eating and drinking before testing. After the washout period, the test subjects provided a baseline tongue bacteria sample by swabbing a side of the back of the tongue with a sterile cotton swab. The test subjects brushed their teeth with a fluoride dental cream (see Table 1) for one minute with the toothbrush having the above-noted tissue cleanser. Subsequently, the test subjects cleaned their tongue surface with a preferred construction of the tissue engaging elements 300 of the toothbrush 100 for ten seconds. Two hours after the cleaning of the tongue surface, a tongue bacteria sample was taken from a side of the back of the tongue with a cotton swab. In the illustrative example, use of the tissue engaging elements controlled more odor causing tongue bacteria than simply brushing the teeth alone. Use of the tissue cleanser 300 demonstrated a tongue bacteria log reduction of over 0.8 Log colony forming units/ml two hours after use on the tongue.

EXAMPLE 3

In another study of the above-noted toothbrush, a MTT assay was used to examine the viability of the epithelial cells collected from the oral cavity prior to and after the use of the toothbrush with the noted tissue cleanser. The MTT Assay was based on the enzymatic reduction of the tetrazolium salt MTT [3-(4,5-dimethylthiazol-2-yl)-2,5-diphenyl-tetrazoliumbromide++ +] in living, metabolically active cells. The reaction was carried out in situ in test tubes, and the reaction product, a purple-colored formazan soluble in dimethylsulfoxide, was measured colormetrically using a multiwell plate reader. Advantageously, the MTT Assay offers a high degree of precision, ease of use, and suitability for the purpose for large scale chemosensitivity testing.

Following a 7-day washout period, the test subjects reported to a test site without prior eating, drinking, or performing oral hygiene. The test subjects provided salivary rinse samples by rinsing their oral cavity with 9 ml of sterile water for 10 seconds and then discharging the water from the rinse into a tube containing 10x sterile phosphate buffered saline(PBS) solution. The samples were refrigerated for approximately 30 minutes before the NITT Assay was run. The test subjects brushed their teeth under supervision for one minute using a fluoride dental cream (see Table 1) followed by 10 seconds of tongue cleaning with the tongue cleanser 300 of the preferred construction. Approximately 30 minutes after brushing and tongue clearing, the test subjects provided a rinse sample in the manner described previously.

The pre-rinse samples and post-rinse samples were centrifuged for 15 minutes at about 3000 RPM. The supernatant, e.g., clear liquid, was removed and the pellet was resuspended in 2.5 mL of PBS. The samples were vortexed for 5 seconds, then 2.5 ml of MTT Solution was added. The samples were subsequently incubated in a gently shaking waterbath set at 37° C. for 2 hours. Following the 2 hour incubation period, the samples were centrifuged for 15 minutes at about 3000 RPM. The supernatatant was siphoned out and 3 mL of detergent (0.04 N Acid Isopropanol) was added to dissolve purple crystals. An increase or decrease in MTT conversion was spectrophotometrically quantified. From each sample, 200 µl of each was added to 96 well plates and the optical density was measured at 570 nm and compared to a negative buffer control. In the illustrative example, one minute of brushing followed by 10 seconds of use of the tissue cleanser reduced oral epithelial cells about 72% as determined by a MTT assay protocol.

EXAMPLE 4

In another study, human test subjects provided baseline VSC samples via a Halimeter™ (i.e., a sulfide meter). A Halimeter™ uses an electrochemical, voltammetric sensor which generates a signal when it is exposed to VSC such as, sulfide and mercaptan gases and measures the concentration of hydrogen sulfide gas in parts per billion. The test subjects brushed their teeth under supervision for one minute with the preferred construction of a toothbrush having the above noted tissue cleanser. Then, the test subjects used the noted toothbrush to provide six strokes on the tongue surface. A subsequent VSC sample was taken from the test subjects two hours after the brushing stage. In this illustrative example, use of a toothbrush with the tissue cleanser reduced the measured VSC in the mouth odor over 35% from a baseline measured two hours after use.

EXAMPLE 5

In one other study, after a washout period, human test subjects rinsed their mouths with sterile water to provide a baseline sample for viable epithelial cell analysis with the MTT assay. The subjects brushed their teeth under supervision for one minute with the preferred construction of the toothbrush having the above-noted tissue cleanser. Then, the test subjects used the tissue cleanser to provide six strokes on the tongue surface. The test subjects provided a post rinse sample for analysis. The samples were tested and analyzed in the manner as discussed with respect to Example 3. In this example, use of the toothbrush reduced oral epithelial cells by about 92% from a baseline as determined by MTT assay protocol.

In the above noted examples, the subjects brushed their teeth using a fluoride dental cream with the formulation in Table 1.

TABLE 1

| % wt. | Ingredient |
|---|---|
| 48.76% | Dicalcium Phosphate Dihydrate |
| 22.0063% | Water |
| 22.00% | Glycerin |
| 4.138% | SO3 Sodium Lauryl Sulfate base - 29% |
| 1.000% | Sodium CMC - 7MF - Food Grade |
| 0.89% | 105 Dental Cream Flavor |
| .76% | Sodium Monofluorophosphate |
| .25% | Tetrasodium Pyrophosphate |
| .20% | Sodium Saccharin |

What is claimed is:

1. An oral care implement comprising:
a handle and a head, the head including a port, the head having a side including a cavity, a resilient tissue engaging region having a pad portion with a plurality of nubs extending therefrom and for removal of debris from an oral soft tissue surface, the pad portion and the port being disposed within the cavity;
the head having an opposite side including a plurality of the tooth cleaning elements extending therefrom, one of the tooth cleaning elements being a bristle; and at least one of the tooth cleaning elements is unitary with the pad portion and the nubs, and extends through the port; wherein the unitary tooth cleaning element is adjacent to the bristle for cleaning teeth.

2. The oral care implement according to claim 1, in which the nubs are conically shaped.

3. The oral care implement according to claim 2, in which the pad portion, the unitary tooth cleaning element and nubs are composed of an elastomeric material.

4. The oral care implement according to claim 1, in which the pad portion, the unitary tooth cleaning element and nubs comprise the same elastomeric material.

5. The oral care implement according to claim 1, wherein the port further comprises a plurality of ports and wherein unitary tooth cleaning elements extend through respective ports.

6. The oral care implement according to claim 1, wherein the unitary tooth cleaning element has a generally concave surface facing the bristle.

7. The oral care implement according to claim 1, wherein the port further comprises a plurality of ports disposed in the cavity and wherein unitary tooth cleaning elements extend through corresponding ports; wherein the unitary tooth cleaning elements generally surround the bristle.

8. The oral care implement according to claim 7, wherein at least one of the unitary tooth cleaning elements has a concave configuration with respect to the bristle.

9. The oral care implement according to claim 7, wherein the pad portion, nubs and unitary tooth cleaning elements comprise the same elastomeric material.

10. The oral care implement according to claim 1, wherein the tissue engaging region has a hardness within the range of about 8-25 Shore A.

11. The oral care implement according to claim 1, in which the nubs are disposed in longitudinal rows and transverse rows on the surface area of the tissue engaging region.

12. The oral care implement according to claim 11, in which adjacent transverse rows of nubs are in a staggered relationship.

13. The oral care implement according to claim 1, wherein the port further comprise a plurality of ports and wherein unitary tooth cleaning elements extend through corresponding ports; wherein the unitary tooth cleaning elements are disposed on opposing sides of an longitudinal axis of the head.

14. An oral care implement comprising a handle, a head, a plurality of elastomeric tooth cleaning elements and a bristle tooth cleaning element extending from one side of the head, and an elastomeric tissue cleanser disposed on an opposite side of the head in a basin having a sidewall portion, wherein said elastomeric tooth cleaning elements are formed as a unitary member with the tissue cleanser; wherein the head includes apertures in the basin; the elastomeric tooth cleaning elements are connected to the tissue cleanser thorough corresponding apertures, the tissue cleanser including a base having a plurality of projections extending from the base.

15. An oral care implement according to claim 14, wherein the projections are conical.

16. An oral care implement according to claim 14, wherein the tissue cleanser has a hardness of about 8-25 Shore A.

17. The oral care implement according to claim 14, wherein the tissue cleanser is composed of SEBS.

18. The oral care implement according to claim 14, wherein the tissue cleanser has about 100-600 projections per square inch.

19. The oral care implement according to claim 14, in which the projections are disposed in longitudinal rows or transverse rows on the base.

20. The oral care implement according to claim 14, wherein the elastomeric tooth cleaning elements are disposed on opposing sides of an longitudinal axis of the head.

21. The oral care implement according to claim 14, wherein the projections of the tissue cleanser are configured for removing oral epithelial cells.

* * * * *